(12) United States Patent
Cain (10) Patent No.: US 9,155,564 B2
(45) Date of Patent: Oct. 13, 2015

(54) SPINE STABILIZATION SYSTEM AND METHOD

(75) Inventor: Christopher Marden John Cain, Eastwood Sa (AU)

(73) Assignee: DePuy Synthes Products, Inc., Raynham, MA (US)

( * ) Notice: Subject to any disclaimer, the term of this patent is extended or adjusted under 35 U.S.C. 154(b) by 44 days.

(21) Appl. No.: 13/119,555

(22) PCT Filed: Sep. 16, 2009

(86) PCT No.: PCT/US2009/057119
§ 371 (c)(1),
(2), (4) Date: Mar. 17, 2011

(87) PCT Pub. No.: WO2010/033567
PCT Pub. Date: Mar. 25, 2010

(65) Prior Publication Data
US 2011/0166601 A1    Jul. 7, 2011

Related U.S. Application Data

(60) Provisional application No. 61/099,019, filed on Sep. 22, 2008.

(51) Int. Cl.
*A61B 17/70* (2006.01)
(52) U.S. Cl.
CPC ......... *A61B 17/7022* (2013.01); *A61B 17/7046* (2013.01)
(58) Field of Classification Search
CPC ........................ A61B 17/7022; A61B 17/7046
USPC .................................................. 606/246–279
See application file for complete search history.

(56) References Cited

U.S. PATENT DOCUMENTS

| 4,269,178 | A  | * | 5/1981  | Keene ........................... 606/276 |
| 4,361,141 | A  | * | 11/1982 | Tanner .......................... 606/252 |
| 4,641,636 | A  | * | 2/1987  | Cotrel .......................... 606/250 |
| 5,549,607 | A  |   | 8/1996  | Olson et al. |
| 2005/0171540 | A1 |   | 8/2005 | Lim et al. |
| 2005/0261685 | A1 | * | 11/2005 | Fortin et al. ..................... 606/61 |
| 2006/0015099 | A1 | * | 1/2006 | Cannon et al. ................... 606/61 |

FOREIGN PATENT DOCUMENTS

| JP | 2002-095674 | 4/2002 |
| RU | 2086200 C1 | 8/1997 |
| SU | 506402 A1 | 3/1976 |

(Continued)

OTHER PUBLICATIONS

Russian Patent application No. 2011115808: English language translation of Decision on Grant dated Nov. 28, 2013, 5 pages.

*Primary Examiner* — Jerry Cumberledge
*Assistant Examiner* — Nicholas Plionis
(74) *Attorney, Agent, or Firm* — Baker & Hostetler LLP (57) ABSTRACT

A stabilization system for the spine that includes an elongated member, preferably an elastic cord, and a plurality of attachment mechanisms, preferably lamina hooks. The stabilization system is configured to extend across a plurality of spinal motion segments to dynamically couple the motion segments in a manner that places the system in tension to apply a compression force to the posterior of the spine. The system and method may have particular application after a laminectomy or laminoplasty procedure.

14 Claims, 7 Drawing Sheets

(56) References Cited

FOREIGN PATENT DOCUMENTS

| WO | WO 00/64360 | 11/2000 |
| WO | WO 2006/101898 | 9/2006 |
| WO | WO 2007/087535 | 8/2007 |
| WO | WO 2007087535 A2 * | 8/2007 |
| WO | WO 2008/013892 | 1/2008 |
| WO | WO 2010/033567 | 3/2010 |

* cited by examiner

SPINE STABILIZATION SYSTEM AND METHOD

CROSS-REFERENCE TO RELATED APPLICATIONS

This application is the National Stage of International Application No. PCT/US2009/057119, filed Sep. 16, 2009, which claims the benefit of U.S. Provisional Application No. 61/099,019, filed Sep. 22, 2008, the disclosures of which are incorporated herein by reference in their entireties for all purposes.

FIELD OF THE INVENTION

The present invention relates generally to orthopedics. More specifically, a preferred embodiment of the present invention relates to a system and method for stabilization of a spine.

BACKGROUND OF THE INVENTION

The spinal canal can be narrowed by the formation of bone spurs arising from the back of the vertebral body or the ligament behind the vertebral bodies. This narrowing of the spinal canal referred to as spinal stenosis can compress and damage the spinal cord and nerve roots. It is desirable to relieve this pressure in and to the spinal cord. Laminectomy, laminotomy or laminoplasty procedures are procedures to relieve pain from spinal stenosis by creating more space for the spinal cord and nerve roots.

A laminoplasty is a posterior procedure where the lamina (two small portions of the vertebra that extends posteriorly) is cut to relieve pressure on the spinal cord. Typically, in a laminoplasty procedure, a groove is made on one side of the lamina creating a hinge and the other side of the lamina is cut all the way through. The lamina is then bent open like a door to enlarge the space for the spinal cord and to take pressure off the spinal cord and nerve roots. The tips of the spinous process may be removed to create room for the lamina bones to pull open. Small pieces of bone or plates are then used to reattach the lamina to the vertebrae while holding open (enlarging) the space for the spinal cord.

A laminectomy is a surgical procedure to remove the lamina or bone spurs in the spine while a laminotomy is a surgical procedure to remove part of the lamina. Part or all of the lamina may be removed on both sides of the vertebra, along with the spinous process. Performance of a cervical laminectomy or laminoplasty often results in a resection or disruption of the ligamentum nuchae, which may lead to post-surgery kyphosis. It is desirable to prevent post-surgery kyphosis as a result of a cervical laminectomy or laminoplasty.

BRIEF SUMMARY OF THE INVENTION

The present invention relates generally to orthopedics. More specifically, a preferred embodiment of the present invention relates to an implant system and method for dynamic stabilization of a spine to prevent post-surgery kyphosis and the compromise of the spinal cord as a result of a cervical laminectomy or laminoplasty.

A spinal stabilization system is illustrated and disclosed and includes an elongated element having a first end region and a second end region, and a pair of hook members configured for attaching to the lamina of a vertebrae, one of the hook members attached to the first end region and the other hook member is attached to the elongated member, wherein the hooks are dynamically coupled and configured to be in tension when implanted.

At least one of the hook members is fixedly attached to the elongated member and the other hook member is adjustably attached to the elongated member to change the position of the hook member along the elongated member. Preferably the elongated member is configured to be in tension when implanted and comprises an elastic cord. Preferably, in one exemplary embodiment, the elongated member is capable of applying about zero (0) to about two hundred (200) lbs of tension to the hook members when implanted in the spine, although the elongated member and system is not limited to this range and other larger ranges of tension (and resulting compression to the spine) are contemplated depending upon the desired use of the stabilization system (including spinal and non-spinal uses).

The system may further include a securing mechanism for securing the hook member to the elongated member. The securing mechanism may be fixedly attached to the elongated member and comprise a blocking cap attached to the elongated member to prevent the hook member from sliding off the elongated member. Alternatively, the securing mechanism may be adjustably attached to the elongated member to permit the position of the hook member along the elongated member to be adjusted in situ.

In one embodiment, the hook member may comprise a bore having a shoulder and the system further includes an elastic element wherein the elastic element is received in the bore and surrounds the elongated element positioned at least partially in the bore wherein the elastic element provides tension to the system. The elongated member may include at least one of the group of rigid, relatively inelastic rods and relatively flexible, relatively inelastic cables or wires.

The spine stabilization system in yet a different embodiment may include an elastic, stretchable cord having a first end region and a second end region, a first hook member fixedly attached to the elastic cord, and a second hook member attached to the elastic cord, the second hook member being adjustably positionable along the length of the elastic cord, wherein the elastic cord and pair of hook members are preassembled and the second hook member is adjustably positionable along the length of the elastic cord to adjust the effective length of the elastic cord to control the tension of the system.

The second hook member may be fixedly securable to the elastic cord in situ by one of the group consisting of crimping, bonding, welding, clamping, gluing, press fitting and the use of set screws. The stabilization system may further include a securing mechanism for securing the hook members to the elastic cord. The securing mechanism may comprise a blocking cap for preventing at least one of the hook members from sliding off of the elastic cord and the blocking cap may be attached at a predetermined and fixed position on the elastic cord. The stabilization system may further comprise a securing mechanism for adjustably securing the hook member to the elastic cord so that the position of the hook member on the elastic cord can be changed during the procedure. The stabilization system may include a plurality of preassembled cord and hook members.

The present invention is also directed to a method of stabilizing the spine including providing a spine stabilizing system having an elongated member with a first end region and a second end region, a pair of hook members for attaching to the lamina of a vertebra, wherein the first hook member is attached to the first end region and a second hook member is attached to the elongated member. The method also includes the steps of securing a first hook member to a first lamina of a first vertebra, passing the elongated member beneath the spinous process of a second vertebra, and securing the second hook member to a second lamina of the first vertebra. The method may further include stretching the elongated member to provide tension to the hook members. The method may further include the step of adjusting the effective length of the elongated member. The step of adjusting the effective length of the elongated member may be performed after the hooks are secured to the vertebra. Adjusting the effective length of the elongated member may include adjusting the position of the hook member along the length of the elongated member.

In a different embodiment, the method of stabilizing the spine may include the step of providing a spine stabilization system having an elongated member with a first end region and a second end region, and a pair of attachment mechanisms for attaching to vertebra. The first attachment mechanism is attached to the first end region and a second attachment mechanism is attached to the second end region. The method may further include the steps of securing a first attachment mechanism to a first vertebra, securing a second attachment mechanism to a second vertebra and placing tension on the first and second attachment mechanisms. The method may further include the step of stretching the elongated members to provide tension to the attachment mechanisms. The attachment mechanisms are preferably hooks and the method may further include attaching the first hook to a first lamina and a second hook to a second lamina. The method may further include the step of adjusting the effective length of the elongated member. The step of adjusting the effective length of the elongated member may be performed after the second attachment mechanism is attached to the second vertebra.

The foregoing summary, as well as the following detailed description of the preferred embodiments of the application, will be better understood when read in conjunction with the appended drawings, and is intended to briefly describe the subject matter of the invention and is not intended to provide an extensive or exhaustive account of the invention and thus should not be read in any way as limiting the scope of the invention in any manner.

BRIEF DESCRIPTION OF THE SEVERAL VIEWS OF THE DRAWINGS

For the purposes of illustrating the stabilization system and method of the present application, there is shown in the drawings preferred embodiments. It should be understood, however, that the application is not limited to the precise arrangements, structures, features, embodiments, aspects, methods and instrumentalities shown, and the arrangements, structures, features, embodiments, aspects, methods and instrumentalities shown may be used singularly or in combination with other arrangements, structures, features, embodiments, aspects, methods and instrumentalities. In the drawings.

DETAILED DESCRIPTION OF THE INVENTION

Certain terminology is used in the following description for convenience only and is not limiting. The words "right", "left", "lower", "upper", "above", "below", "top" and "bottom" designate directions in the drawings to which reference is made. The words "inwardly" or "distally" and "outwardly" or "proximally" refer to directions toward and away from, respectively, the geometric center of the spine stabilization assembly and related parts thereof. The words, "anterior", "posterior", "superior," "inferior", "medial" and "lateral" and related words and/or phrases designate preferred positions and orientations in the human body to which reference is made and are not meant to be limiting. The terminology includes the above-listed words, derivatives thereof and words of similar import.

Figure 1A:
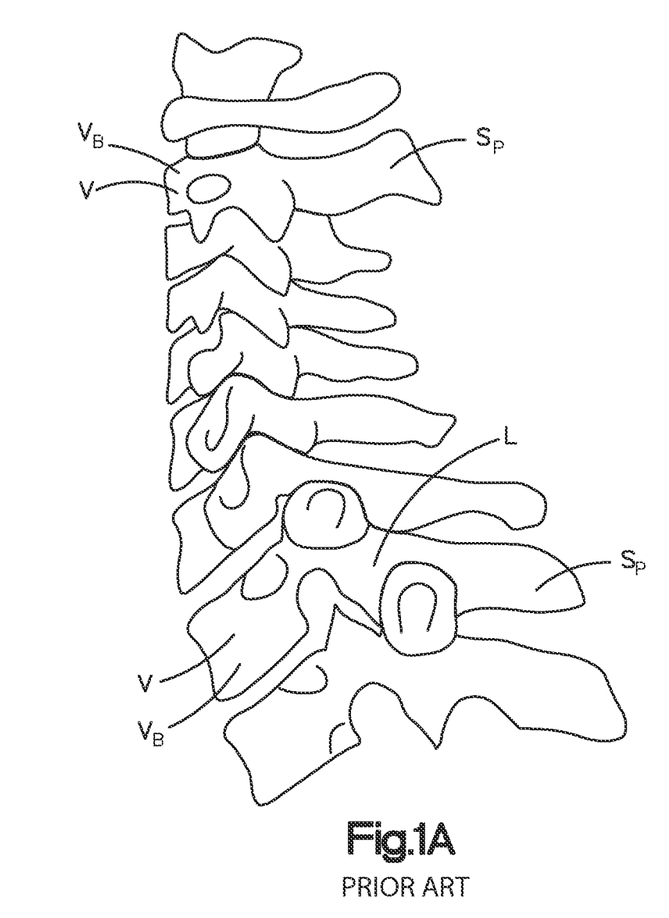
FIGS. 1A-B illustrate a lateral side view and a posterior side view, respectively, of a human spine prior to a laminectomy, laminotomy or laminoplasty procedure.
Figure 1B:
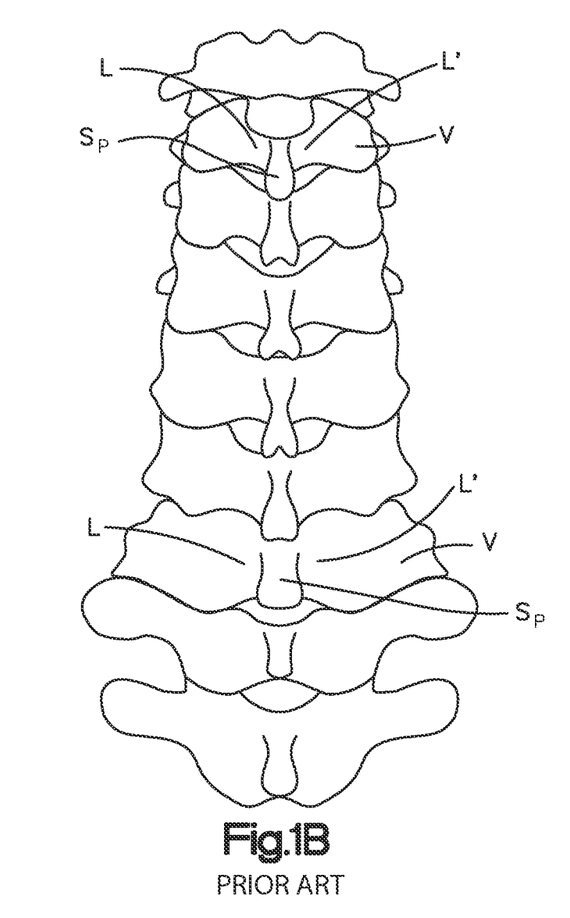
Figure 2A:
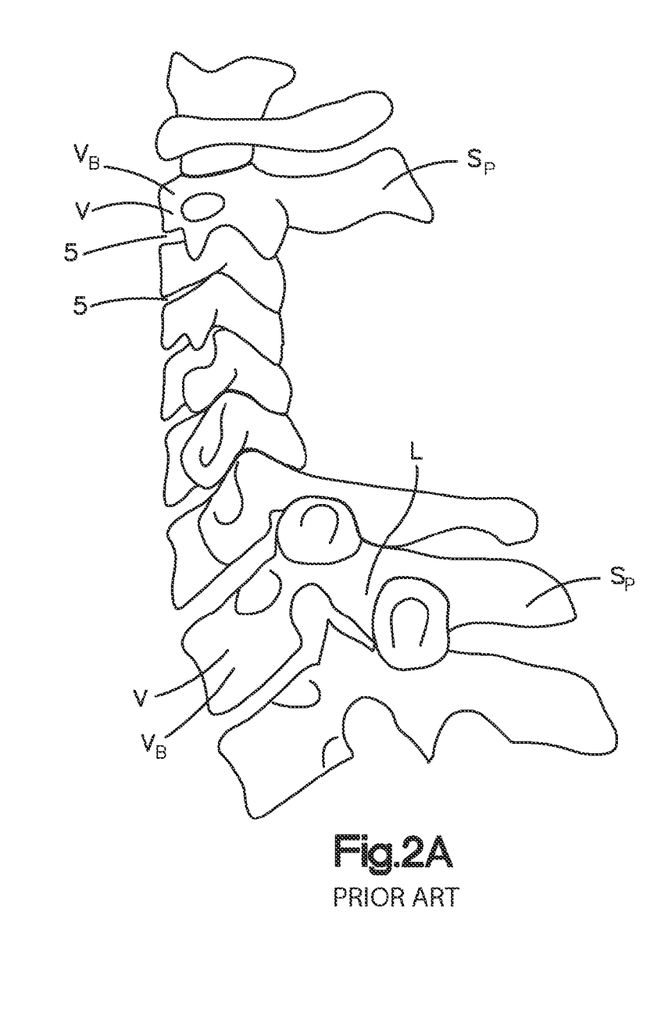
FIGS. 2A-B illustrates a lateral side view and a posterior side view, respectively, of a human spine subsequent to a laminectomy procedure.
Figure 2B:
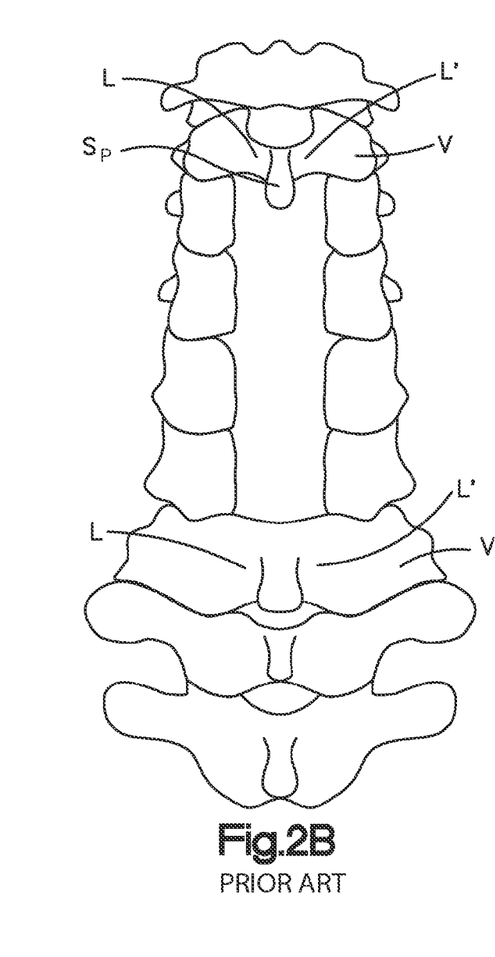
Figure 3:
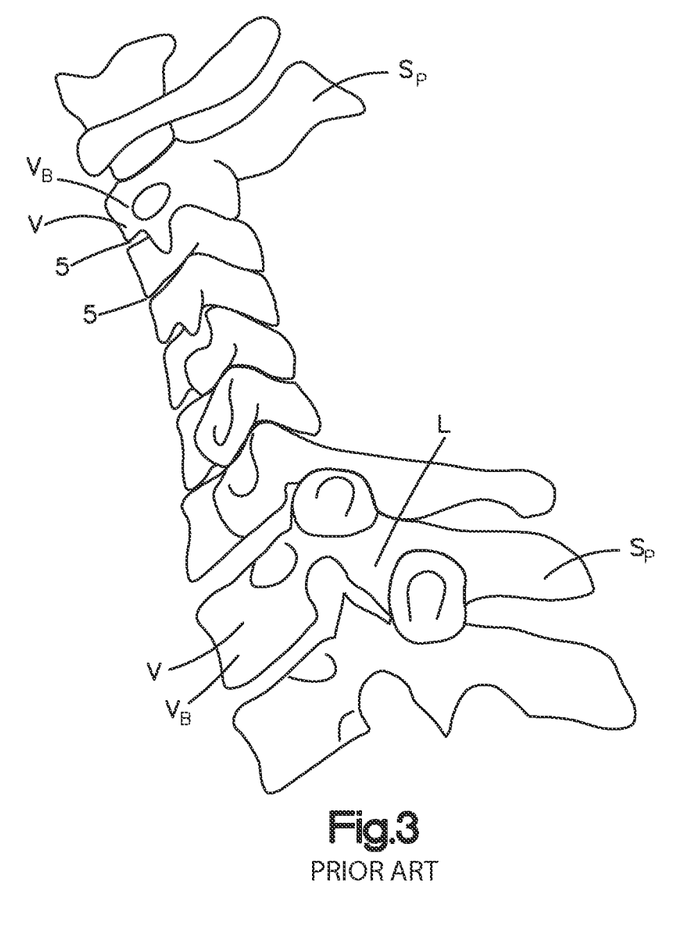
FIG. 3 illustrates a lateral side view of a human spine that has developed post-surgery kyphosis resulting from a laminectomy or laminoplasty procedure.

FIGS. 1A-B illustrate the cervical and portions of the thoracic region of a spine having vertebra V. Each vertebra V includes a vertebral body $V_B$, spinous process Sp, and two lamina L, L', a first lamina L on the right lateral side of the spinous process and a second lamina L' on the left lateral side of the spinous process. The lamina L, L' connect the spinous process SP to the vertebral body $V_B$. Intervertebral discs, and in this example cervical intervertebral discs, are positioned between and separate the vertebral bodies $V_B$. FIGS. 2A-B illustrate the spine after a laminectomy was performed where several levels of cervical vertebra have had their lamina and spinous processes removed. The surgical performance of a cervical laminectomy or laminoplasty procedure however often results in the resection or disruption of the ligamentum nuchae which may lead to post-surgery kyphosis as shown in FIG. 3 and potentially the compromise of the spinal cord. Comparing FIG. 3 to FIG. 2A, the spacing 5 between the vertebral bodies $V_B$ on the anterior side of the spine has decreased and is smaller while the spacing on the posterior side has increased. In FIG. 3, the spine has changed curvature and the cervical region has undertaken a kyphotic angle which can move, manipulate and reposition the spinal cord which can compromise and damage the spinal cord and nerve roots.

Referring to FIGS. 4-7, a spine stabilization system is provided to resist or prevent post-surgery kyphosis, compromise of the spinal canal and/or damage to the spinal cord and nerve roots. The stabilization system may include one or more elongated members, one or more attachment mechanisms for attaching the elongated members to vertebra and one or more optional securing mechanisms preferably for securing the attachment mechanisms to the elongated members. The securing mechanisms optionally may also permit and provide for adjusting the position of the attachment mechanisms with respect to the elongated member. While the spine stabilization system has been generally described as having a plurality of elongated members, a plurality of attachment mechanisms, and a plurality of optional securing mechanisms, it is contemplated and understood that the system may comprise only one elongated member, one attachment mechanism and no securing mechanisms, with two attachment mechanisms for each elongated member being preferred.

Figure 4A:
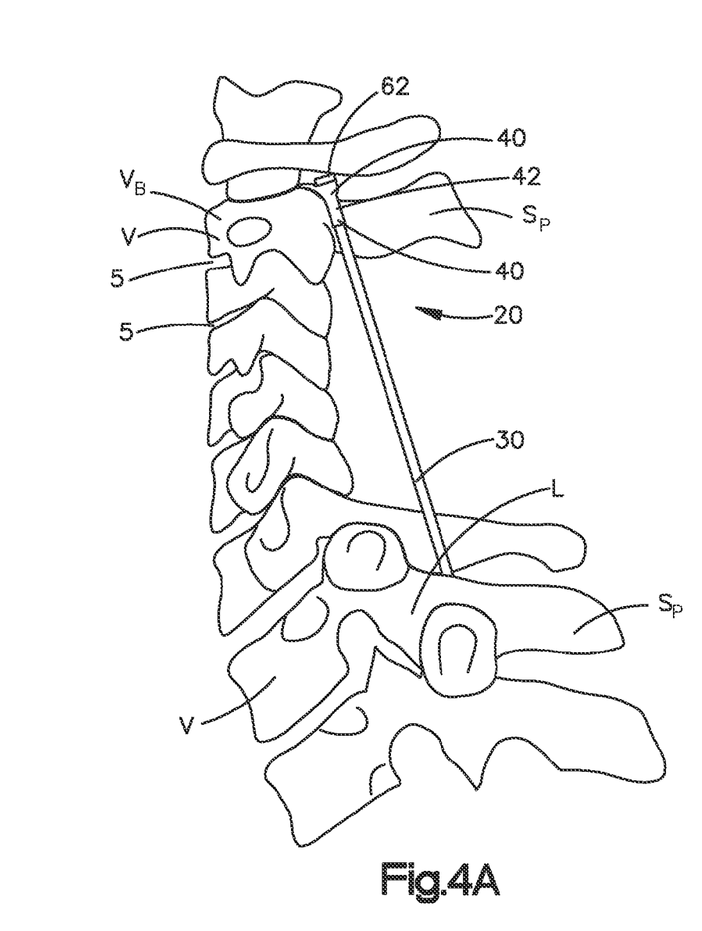
FIGS. 4A-B illustrates a lateral side view and a posterior side view, respectively, of a first preferred embodiment of a stabilization system in accordance with the present invention used on a section of the human spine.
Figure 4B:
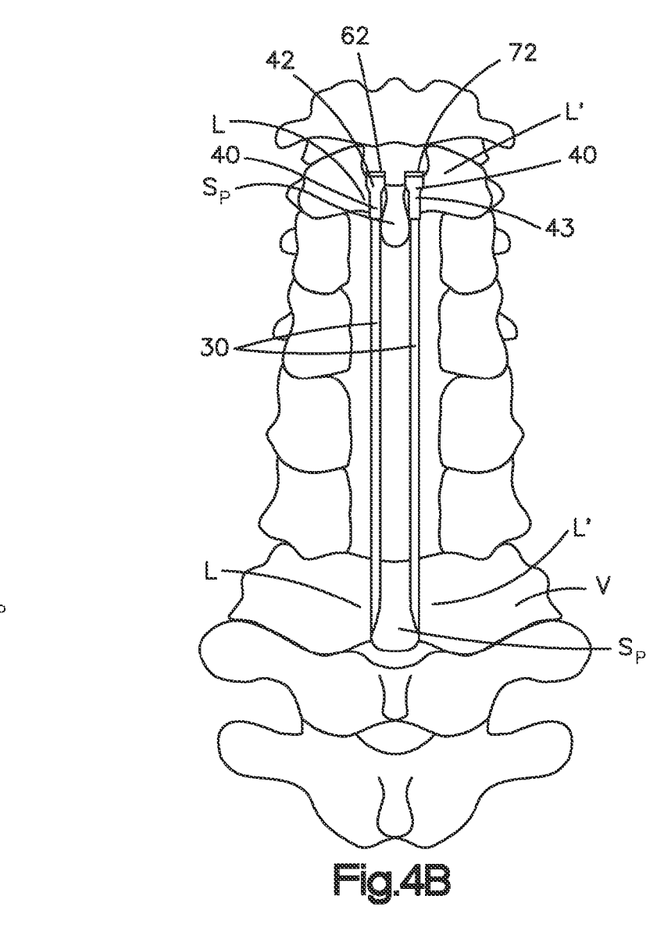
Figure 5A:
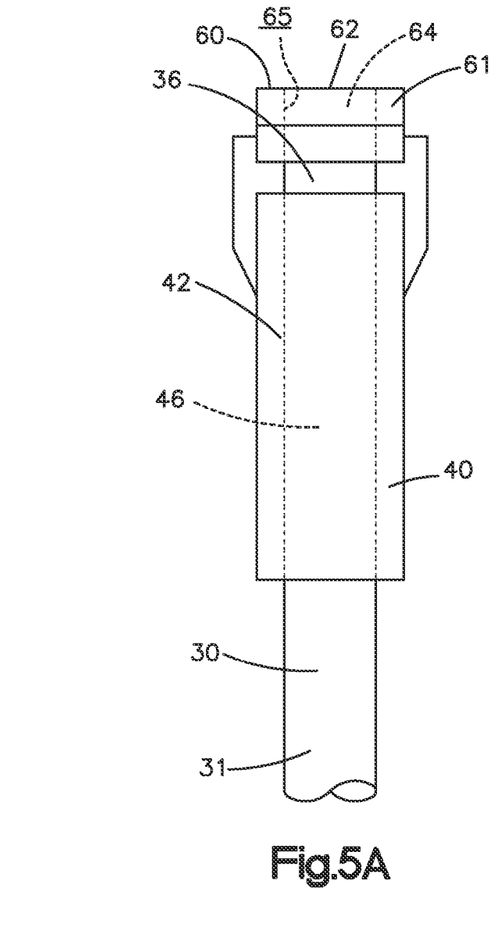
FIG. 5A illustrates a side view of a first embodiment of a hook portion of the stabilization system of FIGS. 4A-B.
Figure 5B:
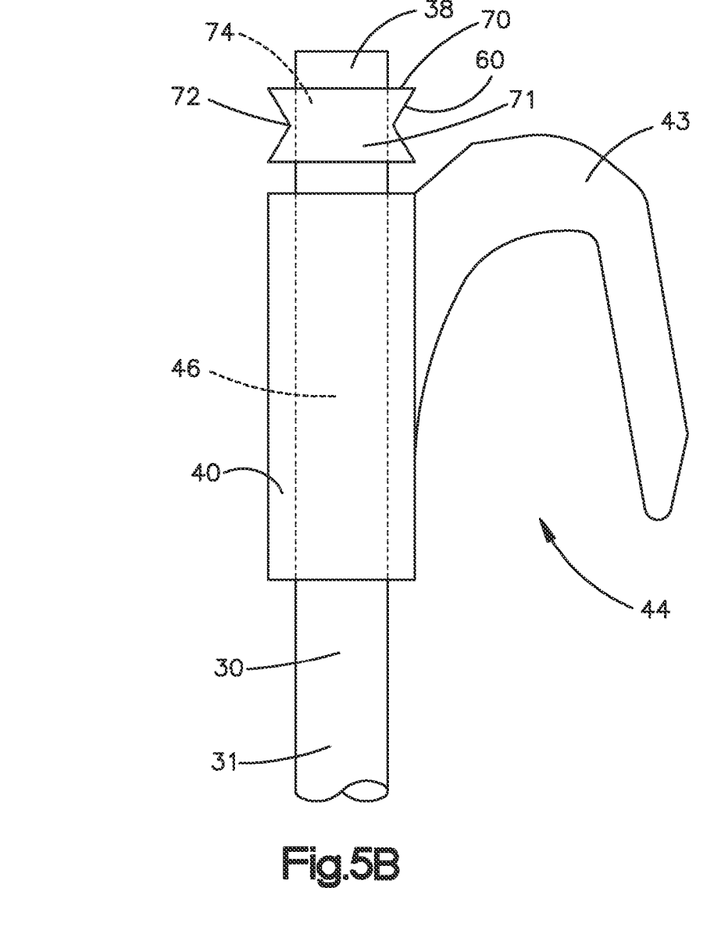
FIG. 5B illustrates a side view of a second embodiment of a hook portion of the stabilization system of FIGS. 4A-B.

Referring to FIGS. 4-5, a first preferred embodiment of a spine stabilization system and method is provided. In the spine stabilization system 20 of FIG. 4, the elongated member 30 preferably is an elastic cord, cable or filament 31 that preferably can stretch and elastically deflect or deform. Elastic cord, cable or filament 31 may be formed of polymers, silicones and/or rubber, such as, for example, silicones, rubber, polyurethanes, and/or PCU, and/or elastic or superelastic metals, such as, for example, Nitinol. Other materials exhibiting the desired elastic properties may also be used, including materials now known or later developed or discovered; and preferably materials that are biocompatible for use in the body.

Figure 6A:
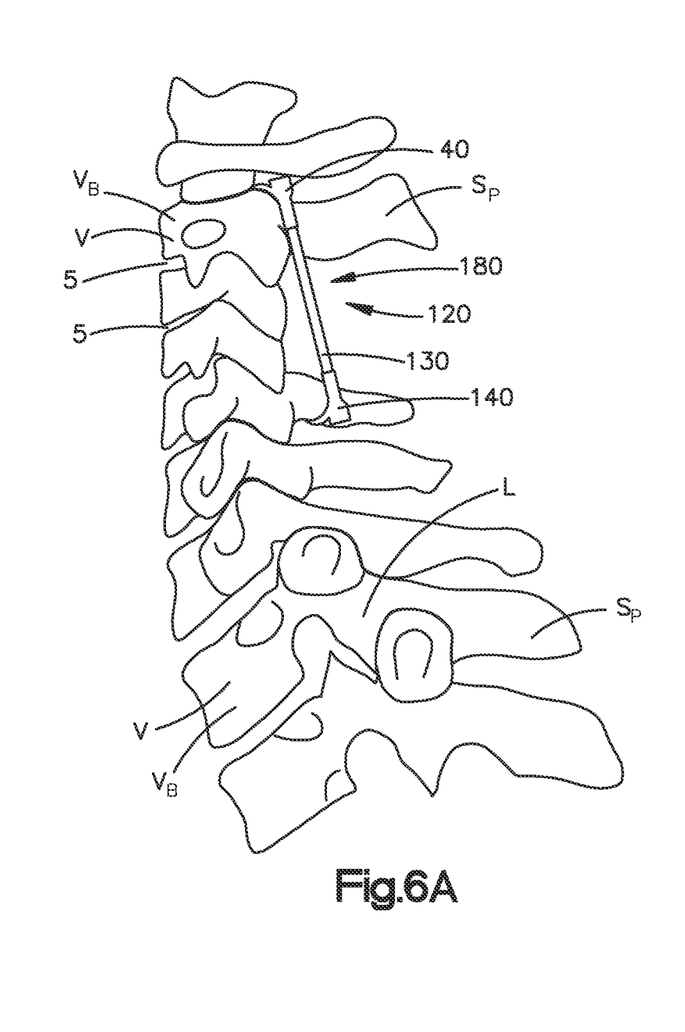
FIGS. 6A-B illustrates a lateral side view and a posterior side view, respectively, of a second preferred embodiment of a stabilization system in accordance with the present invention used on a shorter section of the human spine.
Figure 6B:
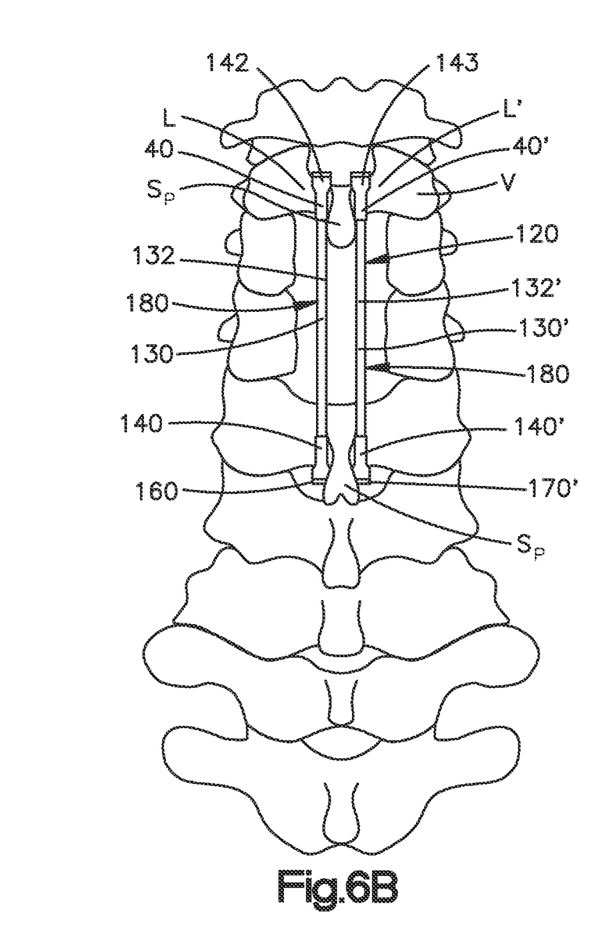

While elongated member 30 is preferably an elastic cord, cable or filament 31, the elongated member may also be a relatively flexible, but relatively inelastic cable or wire 32 (shown in FIG. 6), such as, for example, a metal cable wire 132 formed from materials such as titanium, titanium alloy, stainless steel, or other materials now known or later discovered. The elongated member 30 may also comprise a multifilament cable. The elongated member 30 may also be formed of polymers, composites, carbon fiber, ceramics, Kevlar or a combination of materials now known or later discovered. Alternatively, the elongated member 30 may be a relatively rigid rod 33 (shown in FIG. 7) formed from materials, such as, for example, metal or metal alloys, titanium, titanium alloy, stainless steel, ceramics, composites, or other materials now known or later discovered. The elongated member may comprise a combination of elastic cord segments, flexible cable segments, and/or relatively rigid rod segments. Alternatively or additionally, the elongated member may comprise elastic cord, flexible cable and relatively rigid rod layered or coaxially layered, such as, for example, an elastic material formed over or coating a metal flexible wire cable.

The elongated member 30 may be supplied in different lengths, thicknesses, flexibility, rigidity and elasticity, and a plurality of elongated members 30 may be supplied in a kit providing the user with multiple selections in order to treat a wide variety of patients, circumstances and conditions.

The attachment mechanism 40 in the embodiment of FIGS. 4A-B preferably comprises one or more hooks 42, 43 for engaging the lamina of a vertebra. The hooks 42, 43 preferably have a side opening 44 (shown in FIG. 5B) for fitting over the lamina. Hooks 42, 43 further may include a hollow bore 46 (shown in FIGS. 5A-B) to permit the elongated member 30 to extend through the hooks 42, 43. One or more of the hooks 42, 43 may be attached or secured to the elongated member 30 so that the hooks 42, 43 are permanently retained on, and preferably fixedly attached to, the elongated member 30. Alternatively, one or more of the hooks 42, 43 may be moveably attached or secured to the elongated member 30 so that the position of hooks 42,43 along the length of the elongated member 30 can be adjusted and then fixedly attached to the elongated member 30.

The hooks 42, 43 may be retained on and/or attached to the elongated member 30 in a number of ways. In one embodiment the hook 42 may be crimped onto the elongated member 30 at a desired location along the elongated member 30. The hook 42, 43 may be supplied pre-attached and crimped to the elongated member 30, or the surgeon may place the hook 42, 43 on the elongated member 30, adjust the position of the hook 42, 43 on the elongated member 30 and then crimp the hook 42, 43 to the elongated member 30 during or just prior to the procedure. Alternatively the hook 42, 43 may be pre-attached to the elongated member 30 but moveable and repositionable along the length of the elongated member 30 whereby the surgeon may fixedly secure the hook 42, 43 at a desired location along the elongated member 30 during or prior to the procedure. Numerous attachment mechanisms and means for securing the hooks 42, 43 to the elongated member 30 are contemplated including crimping, bonding, gluing, press-fitting, threading, welding, and/or the use of fasteners, such, as for example, set screws, pins, etc.

While the attachment mechanism 40 has been shown and described as a hook for attaching to the lamina of a vertebra, it should be understood that other attachment mechanisms such as for example, screws, (polyaxial or monoaxial pedicle screws), clamps, pins, etc. preferably attachable to the vertebrae, and preferably to a posterior side of the vertebra are contemplated and feasible.

In the embodiment of FIG. 5A, hook 42 has a bore 46 which receives the elongated member 30 and optional securing mechanism 60 is attached at the first end 36 of the elongated member 30 to secure the hook 42 to the elastic cord 31 and resist or prevent the hook 42 from becoming unattached from the elastic cord 31. The optional securing mechanism 60 may be in the form of a blocking cap 61 which may be crimped onto the first end 36 of the elastic cord 31 and prevent the hook 42 from sliding off of the elastic cord end 36. The blocking cap 61 may prevent the hook from being detached from the elongated member but may permit movement of the attachment mechanism 40 along the length of the elongated member 30 away from the blocking cap 61 and toward the other attachment mechanism 40. When this embodiment is used and the system is placed in tension the attachment mechanism 40 will abut up against the blocking cap 61. Alternatively, as described below the blocking cap 61 may fix or assist in fixing the position of the attachment mechanism with respect to the elongated member 30.

The blocking cap 61 in FIG. 5A may be formed as a hollow circular ring 62 having a hollow interior 64 for receiving the elongated member 30. Alternatively or additionally the ring 62 may have internal threads (not shown) formed on the internal wall 65 which will mate with threads on the elongated member 30 to attach the ring 62 to the elongated member 30. Blocking cap 61 may be preassembled and supplied to hospitals and surgeons fixedly attached to the elongated member 30, or a surgeon or user may attach the blocking cap 61 to the elongated member 30 during or just prior to the surgery. The securing mechanism 60 may be secured to the elongated member 30 by any number of ways and methods including crimping, bonding, gluing, press-fitting, threading, welding, and/or use of fasteners, such as, for example, set screws, pins, etc., or combinations of these securing means. In the embodiment of FIG. 5A, the attachment mechanism 40, specifically hook 42 may move separate from the blocking cap 61. Alternatively or additionally, the blocking cap 61 may couple to the attachment mechanism 40 to retain, hold and fix the position of the attachment mechanism 40 on the elongated member 30. The blocking cap 61 may be preassembled in a coupled state with the attachment mechanism 40 or the attachment mechanism may be coupleable to the blocking cap 61 such that a user can move the attachment mechanism 40 relative to the blocking cap 61 and thereafter couple the attachment mechanism 40 to the blocking cap 61 to fix the position of the attachment mechanism 40.

FIG. 5B shows an alternative securing mechanism 60 formed as an adjustable securing mechanism 70. Adjustable securing mechanism 70 may be an adjustable blocking cap 71 formed as a circular ring 72 having a hollow interior 74 and may be adjustable by a user along the length of the elongated member 30 so that the effective length of the elongated member 30 may be adjusted by the user during the procedure. Unlike ring 62 which is fixedly attached to the end of the elongated member 30, adjustable ring 72 can be moved along the length of the elongated member 30 and thereafter affixed to the elongated member 30 at a desired location so that the effective length of the elongated member 30 used by the system to stabilize the spine can be varied or adjusted during the surgery. The adjustable securing mechanism 70 may be secured to the elongated member 30 in a number of ways that will permit the effective length of the elongated member 30 to be varied and adjusted during the procedure including crimping, welding, bonding, gluing, press fitting, threading and the use of fasteners, such as, for example, set screws, pins, etc., or combinations of these securing means. The blocking cap 71 preferably prevents the attachment mechanism 40 from being detached from the elongated member and permits adjustment of the effective length and control of the tension in the system. Even after the adjustable securing mechanism is fixedly secured to the elongate member, the attachment mechanism 40 may move along the elongated member 30, specifically, move away from the securing mechanism and toward the other attachment mechanism. The blocking cap 71 may also be configured to couple to the attachment mechanism 40 and fix the position of the attachment mechanism 40 along the length of the elongated member 30 when the position of the blocking cap 71 is fixed.

In the embodiments of FIGS. 4A-4B and 5A-B, the first hook 42 is preferably preassembled and attached to the elastic cord 31 by blocking cap 61 which is fixed in position at the first end 36 of the elongated member 30, whereas the second hook 43 is adjustably positionable along the length of the elastic cord 31 by adjusting the position of the adjustable blocking cap 71. In this manner, the spinal stabilization system comprises an elastic cord 31 (or elongated member 30) and two hooks, one pre-attached and the other adjustably attached to the elastic cord 31 and can be used to treat a wide variety of patients. In the embodiment of FIGS. 4A-B, hook 42 is pre-attached, referring to the blocking cap 61 being fixed in position and non-adjustably attached to the elongated member 30, and hook 43 is adjustably attached, referring to the blocking cap 71 being attached to but adjustable along the length of the elongated member 30. It will be appreciated that the spine stabilization system 20 may have two pre-attached securing mechanisms 60 (e.g., blocking caps 61), and/or two adjustably attached securing mechanisms 70 (e.g., blocking caps 71) secured to respective end portions of the elongated member 30.

It can be appreciated that in an embodiment where no optional securing mechanisms are utilized, or in the embodiment where the securing mechanisms are coupled to the attachment mechanisms, the attachment mechanism or securing mechanism can be (1) pre-attached and fixed in position at the end portion, or some intermediate portion, of the elongated member, and/or (2) pre-attached and adjustable along the length of the elongated member. For example, the hook 42 can be pre-assembled and crimped into a fixed position on the elongated member 30 and hook 43 can be retained on elongated member 30 (for example by an enlarged end at the second end 38 of elastic cord 31) and moveable along the elastic cord 31 so that it can be crimped just before or during the procedure. Similarly the spine stabilization system can be supplied with blocking cap 61 crimped and fixed in position on the elastic cord 31 and blocking cap 71 retained on the elastic cord 31 but adjustable along the length of the elastic cord 31 and thereafter fixed in position on the elastic cord 31 whereby hook 42 is coupleable to blocking cap 61 to fix the position of the hook 42 and hook 43 is coupleable to blocking cap 71 to fix the position of the hook 43. Hooks 42, 43 can be coupled to respective blocking caps 61, 71 during manufacture, before the procedure, during the procedure, and/or after blocking cap 71 is adjusted into position, or a combination of these scenarios.

In use, the first end 36 of the elastic cord 31 of the embodiment of FIGS. 4A-B and 5A-B is secured to the lamina via one of the hooks 42, 43 secured to a superior lamina on one side of the spinous process preferably above the laminectomy or laminoplasty. The elastic cord 31 then extends along the spinous process (if a laminoplasty) or extends where the spinous process used to be (if a laminectomy or laminotomy), and is then passed beneath a spinous process to the other side of that spinous process. Elastic cord 31 preferably is passed beneath the spinous process distally preserving the interspinous ligament above and below the laminectomy, laminotomy and/or laminoplasty. The second end 38 of the elastic cord 31 is then secured to the lamina on the other side of the spinous process via the other hook 42, 43 secured to a superior lamina above the laminectomy, laminotomy or laminoplasty. When the second hook 42 or 43 is secured to the lamina, the elastic cord 32 preferably is stretched, taunt and in tension in order to supply a force that compresses the posterior side of the spine to resist and prevent post surgery kyphosis and add stability to the spine.

Preferably the elongated member 30 is an elastic cord 31 which elastically deforms and stretches to increase its length. As the elastic cord 31 is stretched, the amount of tension in the elastic cord increases and the amount of force applied to the section of the spine increases, specifically the amount of force applied to the lamina to which the elastic cord 31 is attached and the spinous process SP about which the elastic cord wraps increases. By adjusting the effective length of the elastic cord 31 a user can adjust the amount the elastic cord 31 stretches and hence the amount of tension when implanting the system in the spine which permits a surgeon or user to adjust and control the amount of compression applied to the posterior side of the spine. Preferably, in one exemplary embodiment, the system applies about zero (0) lbs. to about two hundred (200) lbs. of compressive force to the spine, although the system is not limited to this range of compressive force and other ranges and values of compressive force are contemplated depending upon the system use (spinal or non-spinal) and the surgeon's desire. In the stabilization system 20 with the elastic cord 31 that force is primarily supplied by the elastic cord 31, and preferably by implanting the system such that the elastic cord 31 stretches and is taut or in tension when in an implanted configuration in the spine so that the cord 31 is under tension. The compressive force may be supplied by the elastic cord 31 or other components of the system as discussed below.

In the embodiment of FIGS. 4A-B, preferably only one elastic cord is utilized, two hooks and two blocking caps 61, 71. The blocking cap 61 is preferably preassembled and fixedly attached to the elastic cord 31 at the first end 36. The hook 43 preferably is adjustably attached along the length of the elastic cord 31 by adjustable blocking cap 71 which permits the surgeon or surgical personnel to adjust the effective length and tension of the elastic cord 31. The blocking cap 71 may be supplied on the elongated member 30 in a manner whereby it is non-removably secured to the elongated member 30 but adjustable along the length of the elongated member. Thus, after the first hook 42 is secured to the superior lamina, the elastic cord 31 may be positioned and manipulated as discussed above, the second hook 43 then secured to the lamina, and then the blocking cap 71 adjusted to change the effective length of the elastic cord and/or change the tension in the elastic cord 31 and the system 20, and thereby control the compressive force applied to the posterior side of the spine in the desired region. Alternatively, the length of the elongated member 30, i.e., the elastic cord 31 in this example, may be chosen, adjusted and/or fixed by fixing the position of the blocking cap or second hook 43 and then the second hook 43 attached to the lamina. The blocking caps 61, 71 preferably ease adjustment and securing of the attachment mechanisms 40 to the vertebrae; in this illustrative example, preferably ease adjustment and securing of the hooks 42, 43 to the lamina, L, L'.

Preferably, the elongated member 30 is applied to the spine following a laminectomy, laminotomy or laminoplasty procedure by applying the hooks 42, 43 to a lamina above the laminectomy, laminotomy or laminoplasty and then passing the elongated member 30 beneath the spinous process distally in such a manner that the interspinous ligament above and below the laminectomy, laminotomy or laminoplasty is preserved.

Referring to FIGS. 6A-6B, a second preferred stabilization system 120 is shown which includes a pair of elongated members 130, 130'. The elongated members 130, 130' may be in the form of a relatively flexible but relatively inelastic cable 132, 132' such as, for example, a metal cable formed of titanium, titanium alloy, stainless steel or other relatively inelastic material. The second preferred stabilization system 120 may include superior attachment mechanisms 40, 40' in the form of hooks 42, 43 and may also include an optional pair of inferior attachment mechanisms 140, 140' and an optional pair of inferior securing mechanisms 160, 170' for securing the position of the inferior attachment mechanisms 140, 140' with respect to the elongated members 130, 130'. Inferior attachment mechanism 140 may be the same as hook 42 whereas inferior attachment mechanism 140' may be the same as hook 43. Securing mechanism 160 may be configured and structured the same as blocking cap 61, whereas securing mechanism 170' may be configured and structured to be the same as adjustable blocking cap 71.

The stabilization system 120 may comprise two (2) elongated members each having two (2) attachment mechanisms, one at each end of the elongated member to form two (2) stabilization struts 180. Each stabilization strut 180 preferably includes one attachment mechanism that is fixedly positioned at the end of the elongated member, either directly (for example by crimping) or through a securing mechanism 60, 160 such as, for example, blocking cap 61, and also includes one attachment mechanism that is adjustably positionable along the length of the elongated member, either directly (for example by in-situ crimping) or through an adjustable securing mechanism 70, 170, such as, for example, adjustable blocking cap 71. Each stabilization strut 180 alternatively may include two (2) fixedly attached attachment mechanisms and/or two (2) adjustably attached attachment mechanisms, or combinations thereof. Where combinations of attachment mechanisms are used, the placement of the different attachment mechanisms on either the superior or inferior vertebra would be a matter of surgeon preference. In the embodiment where a relatively flexible but relatively inelastic cable 132 is used for elongated members 130, 130', it is preferred that at least one adjustable attachment mechanism 170' is used in order to adjust the length of and tension in the elongated member 132 when the system 120 is attached to the vertebrae and hence be able to adjust the compression exerted on the posterior side of the spine. While the second preferred embodiment of the spinal stabilization system 120 has been described as using relatively flexible, relatively inelastic cable, it will be appreciated that system 120 and stabilization struts 180 may utilize relatively flexible, elastic cord or a relatively rigid, inelastic rod. Additionally, the attachment mechanisms may be hooks as illustrated and described, alternative hooks, screws, pins, clamps or other fasteners now known or later discovered that are attachable to the spine.

In use, the second preferred spine stabilization system 120 may include one or more spine stabilization struts 180 which may be secured to the spine as follows. The first attachment mechanism 40 may be secured to a first vertebra on a first side of the spine and the second attachment mechanism 140 of the stabilization strut 180 may be secured to a second vertebra on the same side of the spine as the first attachment mechanism with the elongated member 30 extending between the spinal segments that need stabilization, for example, the segments that may have undergone a laminectomy or laminoplasty. Additionally a second strut 180 may be applied in the same or similar manner to the other side of the spine.

The first and second attachment mechanisms of the stabilization strut 180 are preferably secured to the vertebrae in a manner to place the system 120 or stabilization strut 180 in tension so as to apply a compressive force on the spine. One manner or means to place the system in tension is to adjust the effective length of the elongated member after the attachment mechanisms are positioned in the spine, or alternatively to choose an effective length of the elongated member such that when the attachment mechanisms are attached to the spine, the elongated member is in tension and a compressive force is applied to the spine. If two stabilization struts 180 are used the struts 180 can be attached and positioned on both sides of the spine, and then each strut 180 can be adjusted to provide the appropriate tension in the strut 180 and thereby compression to the spine. If the elongated member is an elastic cord or has a section that is stretchable, the elongated member may be stretched to apply tension to the attachment mechanisms. Alternatively, an elastic element can be added to the system, such as, for example, the elastic element 50 discussed below in FIG. 7, which can provide tension to the system.

Figure 7:
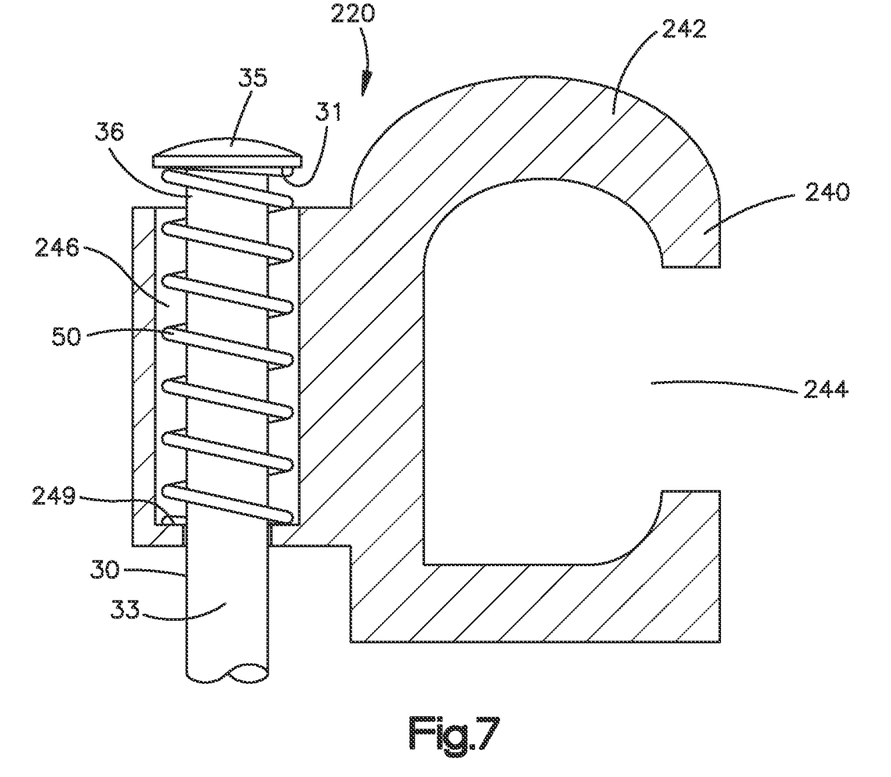
FIG. 7 illustrates a side view of a portion of a third preferred embodiment of a stabilization system in accordance with the present invention.

Referring to FIG. 7, a first end of a third preferred embodiment of a spine stabilization system 220 is provided. Spine stabilization system 220 includes one or more attachment mechanisms 240, one or more elongated members 30 and one or more elastic elements 50. The attachment mechanisms 240 in the stabilization system 220 may include one or more lamina hooks 242 and one or more corresponding elastic elements 50 that couple the hooks 242 to the elongated member 30. Lamina hook 242 includes a hook portion with an opening 244 to receive the lamina of a vertebra. The lamina hook 242 also includes a bore 246 for receiving the elongated member 30 and elastic element 50. The bore 246 is large enough to receive the elastic element 50 which is received in the bore 246 and permits the hook 242 to slide over the rigid rod 33. The bore 246 includes a shoulder 249 against which the elastic element 50 can act. The elastic element 50, may assume the form of a spring-like element, (e.g., a helical spring as shown in FIG. 7), a polymer spacer, rubber sleeve or bushing, etc., and serves to dynamically couple the hook 242 to the elongated member 30. The elongated member 30 in FIG. 7 is in the form of a relatively rigid rod 33. The rigid rod 33 has a cap or enlarged head 35 on its first end 36. The cap 35 serves to prevent the elastic element 50 and hook 242 from becoming detached from the rigid rod 33, and serves as a shoulder 31 against which the elastic element 50 may act. The elastic element 50 provides a force on the rod 33 to provide tension on the system.

In use the elastic element 50 places the spine stabilization system 220 in tension which preferably places the posterior side of the spine in compression. The elastic element 50 and the elastic cord 31 dynamically couple the attachment mechanisms 40, 240 and allow the force applied to the spine to change in situ. In the embodiment of FIG. 7 where the elongated element 30 is a rigid rod 33, the rigid rod 33 may be formed with a curvature or curved section to slip around and under the spinous process, and or the rod 33 may be formed with a flexible cable section, similar to cable 132 used in FIGS. 6A-B, or an elastic stretchable cord 31 as used in FIGS. 4A-B to slip around and under the spinous process. While one end of the spinal stabilization system 220 has been shown as having hook 242, in FIG. 7 it will be appreciated that the other end of the system, the second end region of the elongated member, may have a hook 242, hook 42, hook 43, an alternative hook or other attachment mechanisms such as screws, clamps, pins and other fasteners now known or later discovered. The attachment mechanism 240 at the other end of spinal stabilization system 220 may incorporate or eliminate elastic element 50.

In addition, while the attachment mechanisms 240 in FIG. 7 have been shown and described as a lamina hook 242 it will be appreciated that other mechanisms and means for attaching the elongated member 30 to the vertebra may be utilized including, but not limited to clamps, screws, pins and other fasteners now known or later discovered.

While it may be preferred to provide the spinal stabilization system preassembled so that the attachment mechanisms are secured to the elongated member, it can be appreciated that the system can be supplied in a kit where a plurality of elongated members of different lengths, thickness, strength, flexibility, and stretchability may be supplied with a plurality of separate attachment mechanisms preferably of different sizes and characteristics which may be attached to the elongated members either before or during the procedure and preferably adjusted in different positions on the elongated member. A plurality of optional securing members may also be supplied with the kit.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

I claim:

1. A method of stabilizing a spine, the method comprising the steps of:
    removing at least a portion of a lamina of a first vertebra so as to define a removed segment of the spine;
    securing a first hook member of a spine stabilizing system to a first laminar portion of a second vertebra that is superior to the first vertebra, the spine stabilization system comprising an elongated member having a first end region and a second end region, the first hook member attached to the first end region, a second adjustable hook member moveably attached to the elongated member, and
    passing the elongated member beneath a spinous process of a third vertebra, the third vertebra being inferior with respect to the first vertebra; and
    securing the second hook member to a second lamina portion of the second vertebra such that the a portion of the elongate member spans the removed segment of the spine.

2. The method of claim 1 further comprising stretching the elongated member to provide tension to the hook members.

3. The method of claim 1 further comprising the step of adjusting an effective length of the elongated member.

4. The method of claim 3 wherein the step of adjusting the effective length of the elongated member is performed after the second hook member is secured to the second lamina portion of the second vertebra.

5. The method of claim 3 wherein adjusting the effective length of the elongated member comprises adjusting the second hook member along a length of the elongated member to a selected position.

6. The method of claim 1, further comprising adjusting the second hook member along the elongated member to a selected position.

7. The method of claim 1 wherein the step of removing at least a portion of the lamina comprises one of a laminectomy, laminoplasty, or a laminotomy.

8. A method of stabilizing a spine, the method comprising the steps of:
    removing at least a portion of a lamina of a first vertebra so as to define a removed segment of the spine;
    securing a first attachment mechanism of a spine stabilization system to a second vertebra, the second vertebra spaced from the first vertebra along a first direction along the spine, the spine stabilization system comprising an elongated member having a first end and a second end spaced from the first end along a central axis, the first attachment mechanism attached to the elongated member, a second attachment mechanism moveably attached to the elongated member between the first attachment mechanism and the second end; and
    securing the second attachment mechanism to a third vertebra, the third vertebra spaced from the second vertebra along a second direction that is opposite to the first direction along the spine such that a portion of the elongate member spans at least a portion of the removed segment of the spine; and
    placing tension on the first and second attachment mechanisms.

9. The method of claim 8 further comprising stretching the elongated member to provide tension to the attachment mechanisms.

10. The method of claim 9 wherein the first attachment mechanism is a first hook, the second attachment mechanism is a second hook, and the method further comprises attaching the first hook to a first lamina and a second hook to a second lamina.

11. The method of claim 8 further comprising the step of adjusting the effective length of the elongated member.

12. The method of claim 11 wherein the step of adjusting the effective length of the elongated member is performed after the second attachment mechanism is attached to the third vertebra.

13. The method of claim 8, further comprising fixing the second attachment mechanism to a selected location on the elongated member.

14. The method of claim 8, wherein the step of removing at least a portion of the lamina comprises one of a laminectomy, laminoplasty, or a laminotomy.

* * * * *